United States Patent [19]

King

[11] Patent Number: 4,907,581

[45] Date of Patent: Mar. 13, 1990

[54] RADIOACTIVE AEROSOL INHALATION APPARATUS

[75] Inventor: Russell W. King, Sierra Madre, Calif.

[73] Assignee: Medi-Nuclear Corporation, Inc., Baldwin Park, Calif.

[21] Appl. No.: 214,014

[22] Filed: Jun. 30, 1988

[51] Int. Cl.⁴ ............................................. A61M 11/00
[52] U.S. Cl. ............................ 128/200.18; 128/200.14
[58] Field of Search ..................... 128/200.18, 200.14, 128/206.22, 909, 654, 658; 604/256

[56] References Cited

U.S. PATENT DOCUMENTS 3,307,552  3/1967  Strawn .................................. 604/256
3,630,196  12/1971  Bird .................................. 128/200.18
4,510,929  4/1985  Bordoni et al. ...................... 128/654
4,741,331  5/1988  Wunderlich ..................... 128/200.15

Primary Examiner—Edgar S. Burr
Assistant Examiner—Aaron J. Lewis
Attorney, Agent, or Firm—James E. Brunton

[57] ABSTRACT

An apparatus for use in respiratory diagnostic procedures and respiratory therapy in the field of medicine. The apparatus of the inventions generates sub-micron size radioactive particles for use in performing ventilation studies of the lungs in a novel manner using a nebulizer and a combination of baffles and a settling chamber which function to remove larger radioactive particles from the mist generated by the nebulizer through impaction, turbulence and sedimentation.

9 Claims, 5 Drawing Sheets

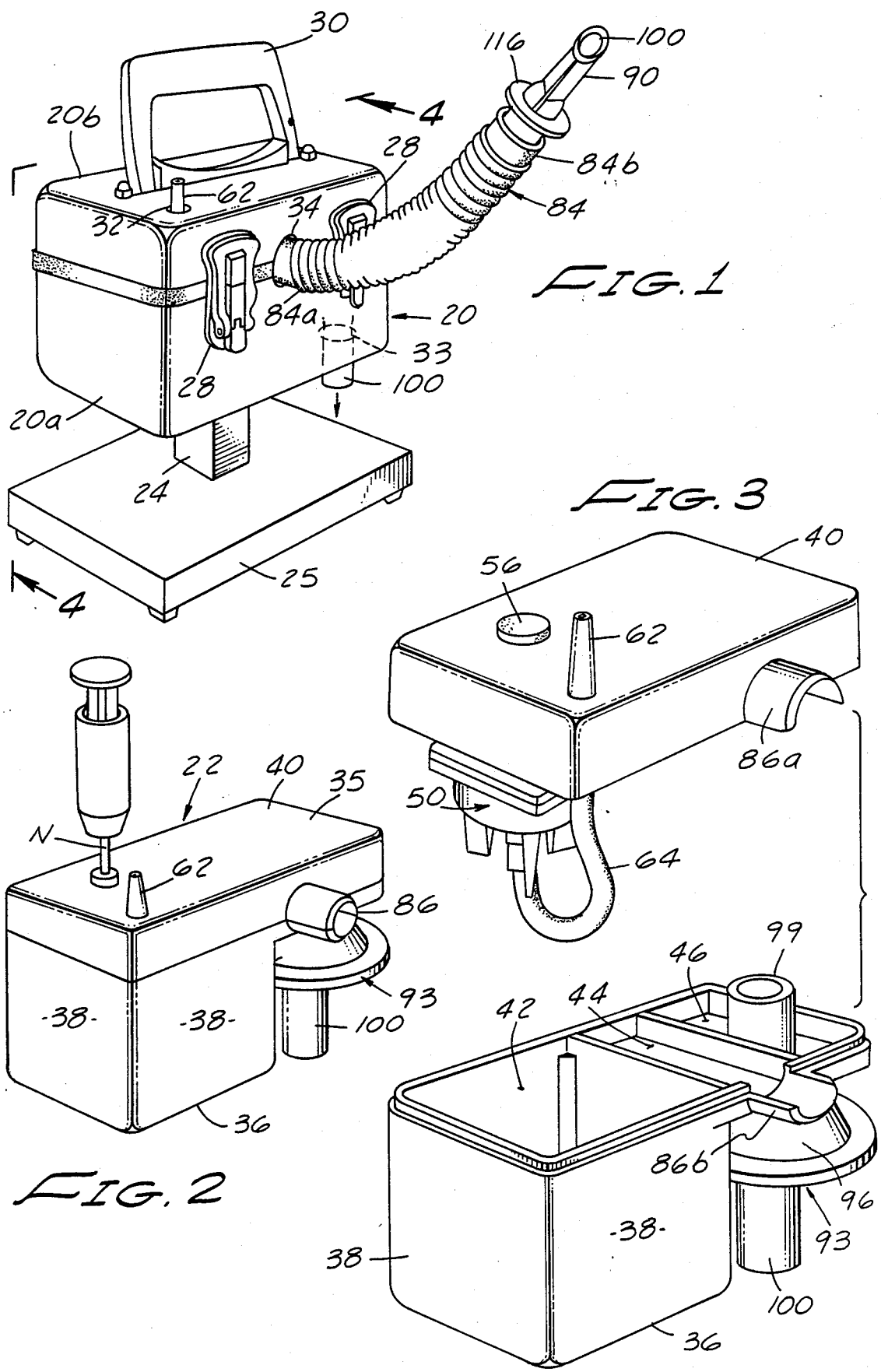

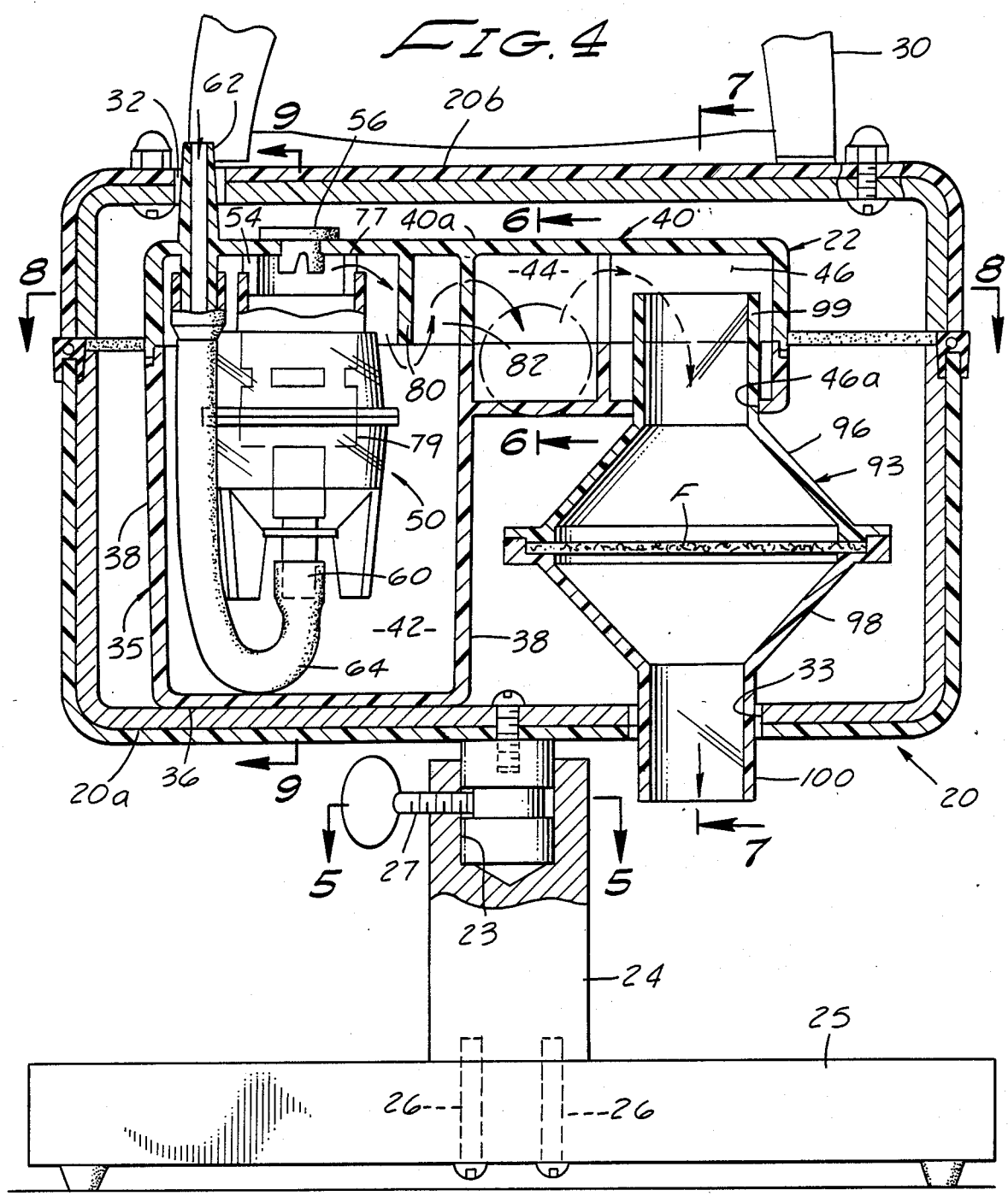

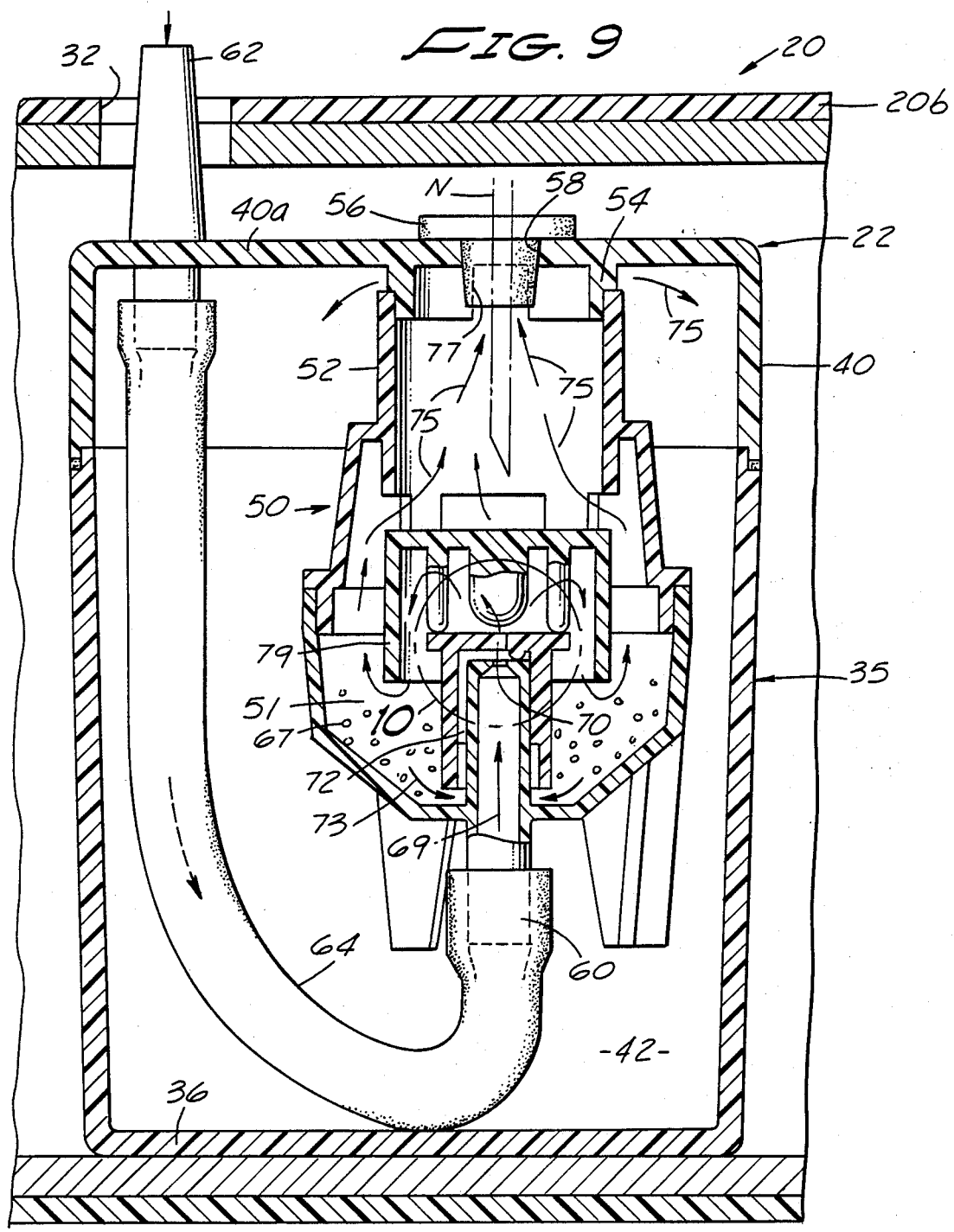
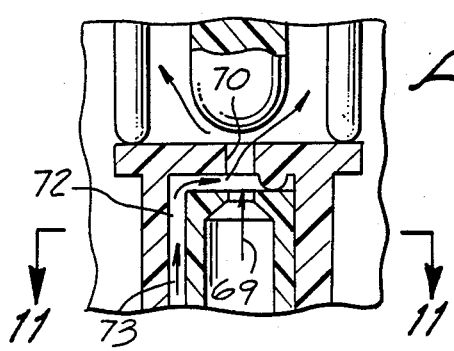
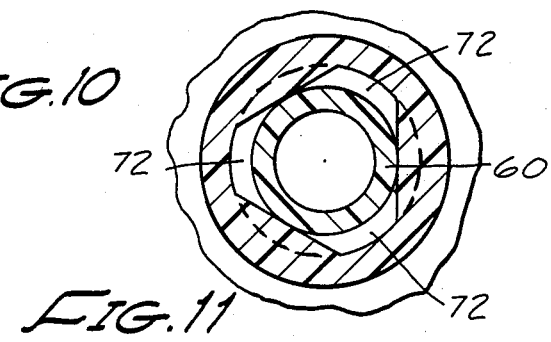

RADIOACTIVE AEROSOL INHALATION APPARATUS

BACKGROUND OF THE INVENTION

1. Field of the Invention

The present invention relates generally to instrumentation of the character used in respiratory diagnostic procedures and respiratory therapy in the field of medicine. More particularly the invention concerns a new and improved aerosol inhalation apparatus that generates sub-micron size radioactive particles for use in performing ventilation studies of the lungs.

2. Discussion of the Prior Art

Various diagnostic procedures involving radioactive materials have been in use for many years in the study of lung functioning. One such procedure involves the injection of Macro-aggregated albuminum (MAA) tagged with radioactive Technetium ($Tc^{99m}$). These particles when trapped in the lungs can be imaged externally with an instrument known as a Nuclear Scintillation Camera, and the resulting images used to determine if any area of the lungs are not functioning properly. In the event of depiction of malfunctioning areas, a question often arises as to whether the cause is due to some type of chronic respiratory disease, or if it is caused by blockage due to emboli. A lung ventilation study is often performed to assist the physician in the differential diagnosis of pulmonary embolism, and to aid in the evaluation of small airway disease.

Historically, ventilation studies have been performed with the use of radioactive gases such as Xenon-133, Xenon-127, and Krypton-81m. More recently techniques have been developed whereby liquids tagged with a radioactive material such as $Tc^{99m}$ can be aerosolized and breathed into the patient's lungs for distribution assessment with scintillation camera imaging. The primary advantage of the aerosol procedure over the use of a radioactive gas is that particles in the aerosol mist are trapped in the lungs rather than being totally exhaled, thereby allowing the imaging of the lungs from various anatomical positions. Disadvantageously, with the radioactive gas method, only one view (usually the posterior) can be taken.

General acceptance of the radioaerosol technique for lung ventilation studies was substantially delayed due to the unavailability of radioaerosol generator-delivery systems designed specifically for diagnostic lung imaging. If particle sizes are large, for example, greater than approximately 2 micron, hyperdeposition of aerosol in the trachea and major airways in patients known to be free of airway obstruction is observed. Also, if particle sizes are large, deposition in the extremities of the lungs is minimal, causing poor visualization on the scintillation camera images. In an attempt to overcome these problems the addition of a "settling bag", was suggested by Dr. George Taplin in the late 1970's. In accordance with this approach, a radioaerosol mist was produced whereby most particles larger than 2 microns were removed. This development resulted in a much wider acceptance of the radioaerosol ventilation study technique. More recently, commercial production of nebulizers producing particle sizes in the range of 1–2 micron have further popularized the general procedure.

An additional refinement called "Pseudogas" was developed in Australia in 1985 and is now undergoing trials at one or more medical institutions here in the United States. This refinement is discussed in an article entitled "Lung Ventilation Studies with Technetium-99m Pseudogas". *Journal of Nuclear Medicine.* 27:842–846, 1986. Although produced only through use of very expensive instrumentation, Pseudogas is receiving very favorable clinical review in that it provides better visualization of the lung periphery with evidence of reduced central airway trapping. In this case, particle size is 0.12 micron diameter which is a order of magnitude smaller than conventional aerosols.

The apparatus of the present invention constitutes a substantial improvement over existing radioaerosol devices providing particle sizes on the order of 0.3 micron, Mass Media Aerodynamic Diameter (MMAD), thereby approaching the particle sizes produced by the "Pseudogas" generator. Although producing particle size approaching that of "Pseudogas", the device of the present invention is an inexpensive, easy to use, multipurpose application unit.

SUMMARY OF THE INVENTION

It is an object of the present invention to provide a disposable radioactive aerosol inhalation apparatus including a lung aerosol unit which both generates and traps sub-micron particles for use in diagnostic pulmonary ventilation studies. More particularly, it is an object of the invention to provide such a unit in which particles on the order of 0.3 micron are generated and trapped.

Another object of the invention is to provide an apparatus of the aforementioned character in which the lung aerosol unit is removably contained within a lead shielded, safety container to minimize radiation exposure to the technologist during operation of the apparatus.

Another object of the invention is to provide an apparatus as described in the preceding paragraph in which the safety container is easily transported and is uniquely designed such that the lung aerosol unit or subassembly, can be quickly, easily and safely removed from the container for disposal.

A further object of the invention is to provide an apparatus of the character described which eliminates the need for one-way valves, thereby reducing patient breathing restrictions to an absolute minimum.

Another object of the invention is to provide a radioactive aerosol inhalation apparatus in which the radioactive liquid to be aerosolized can be easily and safely injected into the lung aerosol unit using a syringe and needle.

Still another object of the invention is to provide a lung aerosol unit which includes a removable breathing tube which extends outwardly from the safety container and terminates in a patient mouthpiece.

Yet another object of the invention is to provide an apparatus as described in the preceding paragraph which includes a removable patient mouthpiece cover or shield, that, when fitted over and around the patient mouthpiece will entrap any saliva contained therein and will effectively prevent external leakage of radioactive and possibly highly contaminated saliva.

Yet another object of the invention is to provide means for safely filtering air exhaled from the patient before its released to room atmosphere.

A BRIEF DESCRIPTION OF THE DRAWINGS

FIG. 1 is a generally perspective view of the radioactive aerosol inhalation apparatus of the present invention.

FIG. 2 is a generally perspective view of the lung aerosol subassembly which is removably contained within the shielded carrying case illustrated in FIG. 1.

FIG. 3 is an enlarged, exploded perspective view of the lung aerosol apparatus shown in FIG. 2.

FIG. 4 is a greatly enlarged view, partly in cross-sectional of the apparatus of the invention taken along lines 4—4 of FIG. 1.

FIG. 5 is a cross-sectional view taken along lines 5—5 of FIG. 4.

FIG. 6 is a cross-sectional view taken along lines 6—6 of FIG. 4 illustrating the manner of interconnection of the breathing tube.

FIG. 9 is an enlarged cross-sectional view taken along lines 9—9 of FIG. 4 illustrating the construction of the nebulizer means of the apparatus.

FIG. 10 is an enlarged cross-sectional view of the area designated by numeral 10 in FIG. 9.

FIG. 11 is a cross-sectional view taken along lines 11—11 of FIG. 10.

DESCRIPTION OF THE INVENTION

Figure 7:
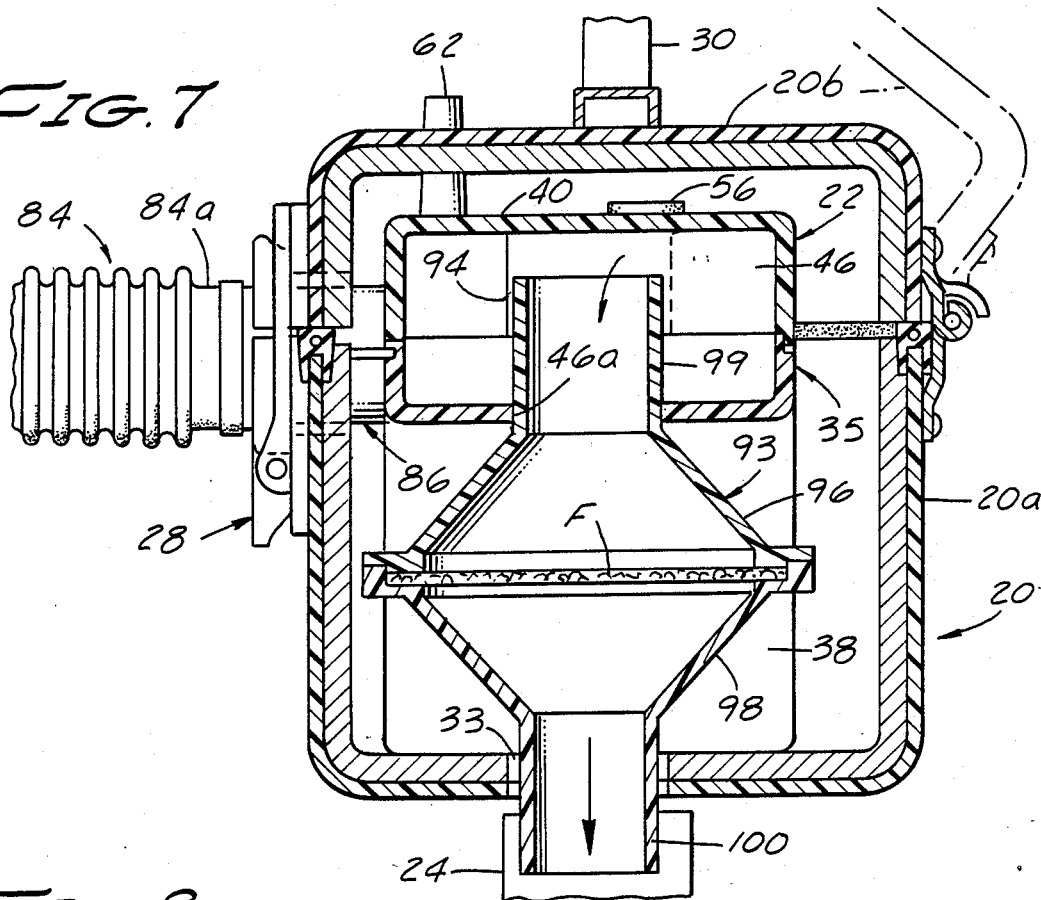
FIG. 7 is a cross-sectional view of the filtering means of the apparatus taken along lines 7—7 of FIG. 4.

Referring to the drawings, particularly to FIGS. 1 through 4, the radioactive aerosol inhalation apparatus of the invention comprises two basic units, namely a shielded portable carrying case 20 (FIG. 1) and a lung aerosol subassembly or apparatus 22 (FIG. 2) which is removably contained within the shielded container or carrying case 20. Container 20 includes a hollow body portion 20a and a hingably connected lid 20b which can be opened to gain access to the lung aerosol apparatus normally carried within container 20.

The top, bottom and side walls of container 20 are preferably lined with a heavy metal such as lead to capture radiation emitted from the liquid media contained within the lung aerosol apparatus 20. For convenience of use, container 20 includes a base connector member 21 (FIG. 4), which is removably received within a counter bore 23 provided in a pedestal 24 which, in turn, is interconnected to a generally rectangularly shaped base member 25 by fasteners, such as screws 26. A set screw 27 secures the base connector member 21 within counter bore 23 (see FIG. 5). Lid 20b of the container is maintained in a closed position by a pair of suitable, cam operated latching devices 28. For ease of portability, a carrying handle 30 is pivotally mounted on lid 20b of container 20. Additionally container 20 is provided with first, second and third apertures 32, 33 and 34 the purpose of which will presently be described.

Figure 8:
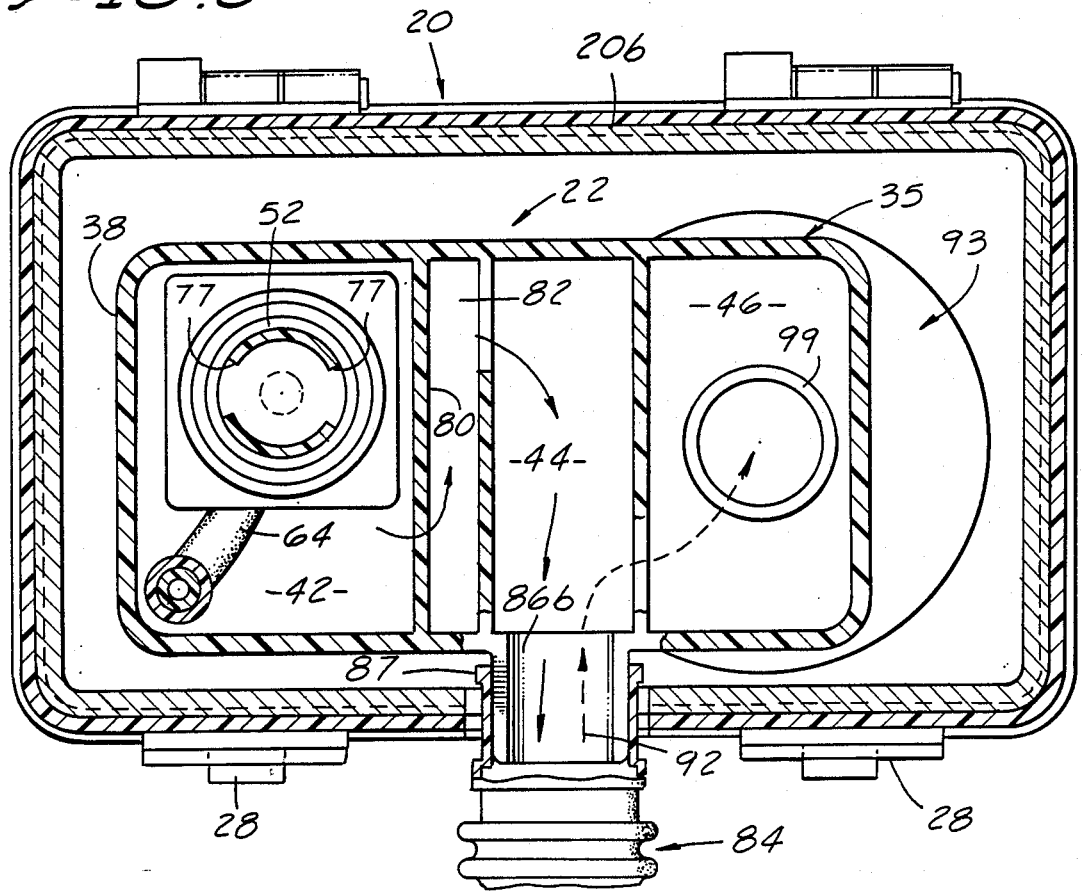
FIG. 8 is a cross-sectional view taken along lines 8—8 of FIG. 4 illustrating the fluid flow paths within the lung aerosol apparatus.

Turning particularly to FIGS. 2, 3 and 4, the lung aerosol subassembly or apparatus 22 comprises a housing 35 having interconnected bottom and side walls 36 and 38 respectively and a removably interconnected top assembly 40. As best seen by referring to FIGS. 3 and 4, housing 35 is provided with first, second and third internal chambers 42, 44 and 46 respectively. Chambers 42, 44 and 46 are interconnected by fluid flow passageways which permit fluid flow from first chamber 42 to second chamber 44 and from second chamber 44 to third chamber 46. Referring particularly to FIGS. 4 and 8 it is to be observed that the fluid flow passageways are intentionally circuitous to control fluid flow generally in the direction indicated by the arrows of FIGS. 4 and 8. The purpose and details of construction of these fluid flow passageways will be described in greater detail in the paragraphs which follow.

Referring to FIGS. 4 and 9, nebulizing means, shown here in the form of a nebulizer 50, is mounted within first chamber 44 for nebulizing a fluid to produce a fine particle laden spray having large and small particles contained therewithin. Nebulizer 50 is of a construction well known to those skilled in the art and low volume nebulizing units of the general character shown in the drawings are readily commercially available. As indicated in FIG. 9, nebulizer 50 includes an upper cylindrical collar 52 and a lower liquid reservoir portion 51 disposed within the sump portion of chamber 42. Collar 52 is closely received over a mounting ring 54 which is affixed to and depends downwardly from wall 40*a* of top 40. Carried by wall 40*a* centrally of ring 54 is accessing means for accessing nebulizer 50 to supply fluid containing a multiplicity of radioactive particles to the reservoir portion thereof. In the embodiment of the invention shown in the drawings, the accessing means comprises a self sealing septum 56 which is mounted within an aperture 58 provided in top wall 40*a* of housing 35. Septum 56 is preferably constructed of soft rubber or other suitable material which is readily penetrable by the needle "N" of a hypodermic syringe in the manner shown in FIG. 9.

Nebulizer 50 is provided with gas inlet means including a gas inlet port 60 and a spaced apart a connector 62 which protrudes through aperture 32 formed in carrying case 20. A flexible connector tube 64 interconnects inlet 60 and connector 62. The nebulizer gas inlet means functions to permit the controlled introduction into the nebulizer of a gas under pressure to cause nebulizing of the fluid containing radioactive particles disposed within reservoir 51 of the nebulizer. This particulate containing fluid is generally designated in FIG. 9 by the numeral 67 and may consist of various radioactive materials depending upon the end use to be made of the apparatus. For many end use applications, radioactive Technetium 99M DTPA is used. Other radioactive or non-radioactive solutions can be conveniently introduced into the nebulizer through septum 56 depending upon the type of diagnosis or treatment being undertaken.

In operating the nebulizer 50 a source of gas (not shown) such as oxygen or compressed air is interconnected by a suitable conduit with connector 62. The gas is then applied to the nebulizer at a flow rate of on the order of ten liters per minute through the inlet port 60 via connector 62 and tube 64. As best seen in FIGS. 9 and 10, the gas flowing through the inlet port in the direction of the arrow 69 passes through a very small orifice 70. This causes the liquid 67 to be drawn from reservoir 66 through the passageway 72 in the direction of the arrows 73. Due to the basic design of the nebulizer and in accordance with the Bernoulli effect, the liquid drawn from the reservoir will be predictably converted into a fine mist containing both large and small particles of radioactive material. The fine particulate laden mist will be forced upwardly through the nebulizer unit in the direction of arrows 75 and toward outlet ports 77 (see also FIG. 8). The standard commercially available nebulizer is modified slightly by adding a downwardly depending cylindrical member 79 which surrounds the outlet side of orifice 70 in the manner shown in FIG. 9 so as to increase turbulence within the nebulizer. This functions to reduce the size of the particles reaching the outlet ports 77 and, along with additional baffling means, presently to be described, limits the size of the particles reaching second chamber 44.

Turning to FIG. 4, it is important to note that the particulate laden mist flowing through outlet 77 is uniquely directed toward a baffle 80 which also forms part of the baffling means of the invention. The baffle means, which include baffle 80, function to control the flow of fluid from the small orifice 70 along a baffled, circuitous path leading toward second chamber 44. More particularly it is to be noted that due to the location of the fluid outlet ports 77 of nebulizer, the particulate laden mist flowing through these ports will be directed at right angles toward baffle 80. Bombardment of this jet stream of mist against baffle 80 will cause a further breakdown of the large particles of radioactive material contained within the particulate laden mist and also will cause the particulate laden mist to disperse throughout the volume of chamber 42, including the lower sump portion, which functions as a settling chamber. The unique construction of the baffled settling chamber functions to effectively remove larger particles from the particulate laden mist via sedimentation, impaction and turbulence.

As long as compressed air or oxygen is supplied to the nebulizer through the fluid inlet means and so long as liquid remains in the nebulizer reservoir, a constant supply of mist containing radioactive particles will be directed toward chamber 44. However, due to the unique construction of the apparatus of the invention, including the circuitous passageways and baffling means, the size of radioactive particles reaching the second chamber are extremely small being on the order of 0.31 microns MMAD.

Also forming an important aspect of the lung aerosol apparatus 22 of the invention is inhalation means which is interconnected with second chamber 44 for permitting inhalation of the particle laden fine spray which reaches the second chamber via fluid passageway 82 (FIGS. 4 and 8). Referring particularly to FIGS. 1, 6 and 8, the inhalation means of the present embodiment of the invention includes an elongated tubular breathing hose 84 having proximal and distal ends 84a and 84b respectively. As best seen in FIG. 1, breathing hose 84 extends through aperture 34 provided in container 20. The proximal end 84a of the breathing hose is interconnected with a cylindrically shaped outlet port 86 which is integrally formed with housing 35 proximate the outlet end of chamber 44. As indicated in FIG. 3, cylindrical outlet member 86 is formed in two identical halves with the first half thereof 86a being formed integrally with top assembly 40 and with the lower portion thereof, designated as 86b, being integrally formed with side wall 38 of the lower portion of the housing 35. As best seen in FIG. 6, breathing hose 84 is provided with a tubular connector section 87 which is closely receivable over outlet port 86. Affixed at the distal end 84b of the breathing hose is a patient mouthpiece 90 the details of construction of which are more clearly shown in FIGS. 12 through 14. This construction will presently be described in greater detail.

In using the apparatus of the invention, the patient places the patient mouthpiece 90 in the mouth and breaths normally. During inhalation, the particulate laden mist reaching chamber 44 will be breathed into the patient's lungs. During exhaling the particulate laden mist will be forced in a reverse direction through the breathing hose in the direction indicated by the arrow 92 and will flow from chamber 44 into chamber 46 via a passageway 94 (FIG. 8).

Turning to FIGS. 4 and 7, chamber 46 is provided with an opening 46a within which is mounted filtering means for filtering particles from the particulate laden spray flowing into chamber 46 as a result of exhalation by the patient through the breathing tube 84. In the embodiment of the invention here shown, the filtering means comprises a filtering unit 93 having mateably interconnected upper and lower frustoconically shaped portions 96 and 98 respectively. Formed integrally with portion 96 is a cylindrically shaped inlet member 99 which is secured within aperture 46a of chamber 46 and extends into chamber 46 a limited distance. Similarly, a cylindrically shaped outlet member 100 is integrally formed with frustoconically shaped member 98. Disposed intermediate members 96 and 98 is a filtering element F, such as a porous fabric or felt, for filtering particulate radioactive material from the fluid flowing from chamber 46 through the filtering unit. Filtering element F is of a character well known to those skilled in the art and numerous suitable filtering materials are readily commercially available. As indicated in FIGS. 1 and 7, cylindrical portion 100 of the filtering unit extends through the aperture 33 formed in the base of container 20 so that the filtered fluids passing through the filtering unit are released to atmosphere.

Figure 12:
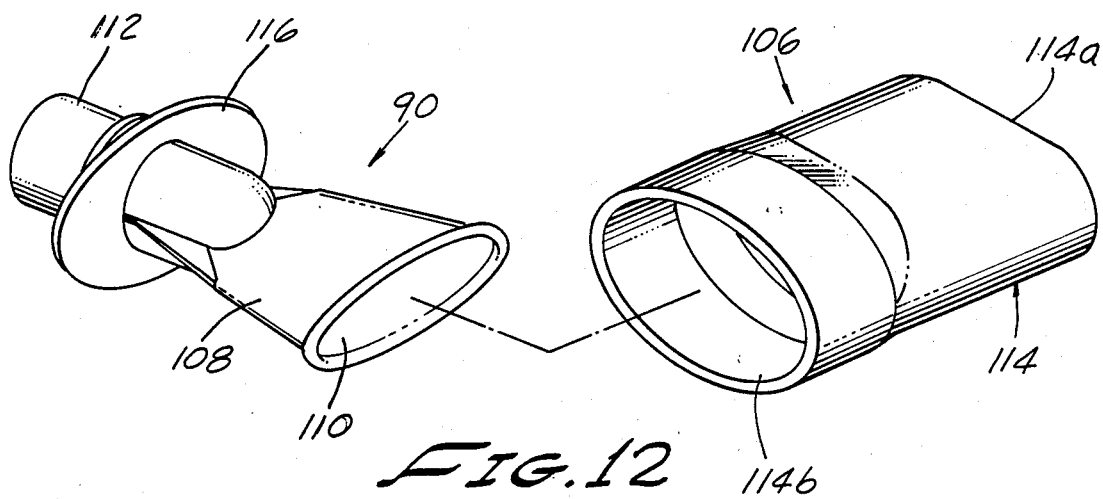
FIG. 12 is a generally perspective view of the patient mouthpiece and cover means of the invention for covering the mouthpiece to prevent the spread of contamination.
Figure 13:
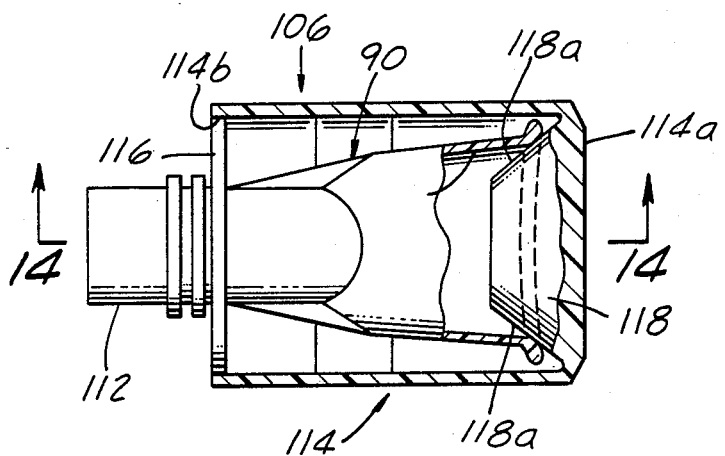
FIG. 13 is a cross-sectional view of the mouthpiece and cover shown in FIG. 12 with the cover in place over the patient's mouthpiece.
Figure 14:
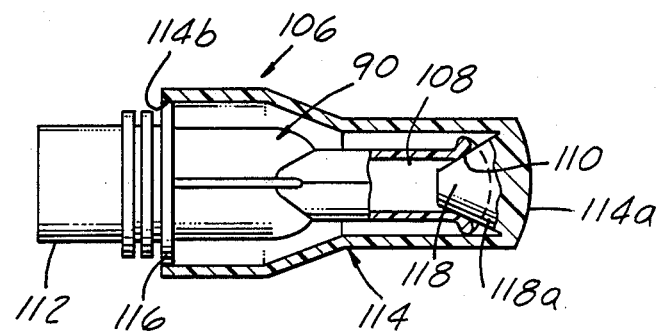
FIG. 14 is a cross-sectional view taken along lines 14—14 of FIG. 13.

Referring to FIGS. 12, 13 and 14 of the drawings the patient mouthpiece enclosure device of the present invention, generally designated by the numeral 106, is designed for removable interconnection with a patient mouthpiece such as the patient mouthpiece 90 shown in FIG. 1. The previously identified patient mouthpiece 90 includes a first hollow portion 108 having an opening 110 at the forward end thereof. Integrally interconnected with first hollow portion 108 is a second tubular portion 112 designed for removable interconnection with the distal end of breathing tube 84. The first portion of the patient mouthpiece may be elliptical in cross-section, as indicated in FIG. 12, or may have various other configurations acceptable for comfortable emplacement within the patient's mouth.

Turning to FIGS. 13 and 14, the enclosure device 106 of the present invention comprises a hollow housing 114 receivable over at least the first portion 108 of the patient mouthpiece 90 and sealing means carried by the hollow housing for sealable engagement with the fluid passageway 110 of the patient mouthpiece. Hollow housing 114 is closed at its forward end by a closure wall 114a and is provided at its opposite end 114b with an opening configured to be closely received over a transversely extending shield-like member, or wall, 116 formed on the patient mouthpiece intermediate first and second portions 108 and 112.

In the embodiment of the invention shown in the drawings, the sealing means comprises a formed, inwardly extending protuberance 118 carried by end wall 114a and disposed internally of hollow housing 114. Protuberance 118 is provided with inwardly tapering side walls 118a which are sealably receivable within opening 110 of the patient mouthpiece 90. As indicated in FIG. 13, the configuration of the protuberance 118 is such that it effectively closes the fluid passageway of the patient mouthpiece and at the same time frictionally engages the opening 110 in a positive manner as to maintain the enclosure device in a fixed position relative to the patient mouthpiece.

While the enclosure device of the invention can be constructed of a variety of materials, in practice, the device is integrally formed of a moldable plastic material such as polyethylene or polypropylene.

In using the enclosure device of the present invention, to encapsulate a mouthpiece possibly contaminated with radioactive saliva, with the mouthpiece still connected to breathing tube 84 the enclosure device is placed over the first hollow portion 108 of the mouthpiece, which portion has been retained within the patient's mouth. As previously mentioned, because the patient has breathed back and forth through the mouthpiece and tubing, varying amounts of saliva have become entrapped in the mouthpiece and in the tubing. By finally urging the enclosure device into engagement with the patient mouthpiece, the sealing means, or protuberance, 118a will be received in, and sealably close, the opening 110 formed in the mouthpiece. At the same time, the transverse wall or shield 116 formed on the patient mouthpiece will enter the open end 114b of the closure device. The fit of the sealing means to the mouthpiece and of the transverse wall 116 to the opening 114b is such that sufficient frictional forces will result to hold the device in the position shown in FIG. 13. In this position the interior of the mouthpiece containing the patient saliva is effectively sealed and the outer surfaces of the patient mouthpiece, which have been retained within the patient's mouth, are completely encapsulated by the housing portion of the enclosure device. In this way, saliva contained in the mouthpiece is retained therewithin and cannot escape from the enclosure device. Further, since the enclosure device encapsulates the portion of the mouthpiece which has been in the patient's mouth, spread of contamination from the surfaces which have been in contact with the patient's mouth is effectively prevented.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A radioactive aerosol inhalation apparatus comprising:
    (a) lung aerosol apparatus including a housing having a first and second adjacently disposed chambers, said first chamber having interconnected side and bottom walls;
    (b) nebulizing means including an upper collar and a lower liquid reservoir portion defined by the inner walls of an outer shell mounted laterally of said first chamber for nebulizing a fluid containing radioactive particles to produce a fine particulate laden spray having large and small radioactive particles, said nebulizing means having exhaust means for causing said particulate laden spray to flow toward said second chamber, said outer shell of said nebulizing means cooperating with said side and bottom walls of said first chamber to define a lower sump portion adapted to function as a settling chamber and separating said reservoir from said lower sump portion;
    (c) a source of gas containing a gas under pressure and conduit means for conducting said gas to said nebulizing means;
    (d) baffle means disposed intermediate said exhaust means of said nebulizing means and said second chamber for interaction with said particulate laden spray flowing toward said second chamber to impede the flow of large radioactive particles toward said second chamber, whereby said large radioactive particles will fall by force of gravity into said settling chamber for entrapment therein; and
    (e) inhalation means in communication with said second chamber for permitting inhalation of spray reaching said second chamber.

2. A radioactive aerosol inhalation apparatus as defined in claim 1 in which said baffle means comprises a transverse wall disposed intermediate said first and second chambers.

3. A radioactive aerosol inhalation apparatus as defined in claim 1 in which said apparatus further comprises a lead lined carrying case for removably receiving said housing therewithin.

4. A radioactive aerosol inhalation apparatus as defined in claim 3 in which said carrying case is provided with an aperture and in which said inhalation means comprises an elongated tubular breathing member having a proximal end connected to said housing proximate said second chamber and a distal end for interconnection with a patient mouthpiece, said patient mouthpiece comprising:
    (a) walls defining a first hollow portion open at one end and receivable within the patient's mouth to form a cavity within which of saliva means or other body fluids can collect;
    (b) a second portion interconnectable with said distal end of said elongated tubular member; and
    (c) a fluid passageway extending between said first and second portions to permit the passage of fluids from said second chamber of said housing through said patient mouthpiece.

5. A radioactive aerosol inhalation apparatus as defined in claim 4 further including cover means removably receivable over said patient mouthpiece, said cover means comprising;
    (a) a hollow housing receivable over at least the first portion of said patient mouthpiece for substantially encapsulating said first portion; and
    (b) sealing means carried by said hollow housing for sealable engagement with said fluid passageway of said patient mouthpiece to prevent body fluids contained within said first portion of said mouthpiece from escaping therefrom.

6. A radioactive aerosol inhalation apparatus as defined in claim 5 in which said sealing means of said cover means comprises a protuberance disposed internally of said hollow housing, said protuberance having inwardly sloping walls movable into sealing engagement with said walls defining said open end of said first hollow portion.

7. A radioactive aerosol inhalation apparatus comprising:
   (a) lung aerosol apparatus including a housing having first, second and third adjacently disposed, side by side chambers, said first chamber having interconnected side and bottom walls and said third chamber having an inlet passageway in communication with said second chamber and an outlet passageway in communication with said second chamber and an outlet passageway in communication with atmosphere;
   (b) nebulizing means including an upper collar and a lower liquid reservoir portion defined by the inner walls of an outer shell mounted internally of said first chamber for nebulizing a fluid containing radioactive particles to produce a fine particulate laden spray having large and small radioactive particles, said nebulizing means having exhaust means for causing said particulate laden spray to flow toward said second chamber, said outer shell of said nebulizing means cooperating with said side and bottom walls of said first chamber to define a lower sump portion adapted to function as a settling chamber and separating said reservoir from said lower sump portion;
   (c) a source of gas containing a gas under pressure and conduit means for conducting said gas to said nebulizing means;
   (d) a baffle wall disposed above said lower sump portion and intermediate said exhaust means of said nebulizing means and said second chamber for interaction with said particulate laden spray flowing toward said second chamber to impede the flow of large radioactive particles toward said second chamber, whereby said large radioactive particles will fall by force of gravity into said settling chamber for entrapment therein; and
   (e) inhalation means in communication with said second chamber for permitting inhalation of spray reaching said second chamber.

8. A radioactive aerosol inhalation apparatus as defined in claim 7 in which said housing includes access means for accessing said nebulizer to supply thereto a fluid containing radioactive particles.

9. A radioactive aerosol inhalation apparatus as defined in claim 8 in which said access means comprises a septum carried by said housing proximate said nebulizing means, said septum being penetrable by the needle of a syringe.

* * * * *